United States Patent [19]

Witucki et al.

[11] 4,419,286

[45] Dec. 6, 1983

[54] AZIDO ESTERS

[75] Inventors: Edward F. Witucki, Van Nuys; Joseph E. Flanagan, Woodland Hills, both of Calif.

[73] Assignee: The United States of America as represented by the Secretary of the Air Force, Washington, D.C.

[21] Appl. No.: 370,235

[22] Filed: Apr. 21, 1982

[51] Int. Cl.$^3$ ............................................. C07C 117/00
[52] U.S. Cl. ...................... 260/349; 149/88; 149/19.1; 149/19.3; 149/19.5
[58] Field of Search .............. 260/349; 149/19.1, 19.3, 149/19.5, 88

[56] References Cited

U.S. PATENT DOCUMENTS

| | | | |
|---|---|---|---|
| 2,769,819 | 11/1956 | Sommers et al. | 260/349 |
| 3,122,570 | 2/1964 | Stansbury, Jr. et al. | 260/349 |
| 3,872,158 | 3/1975 | Marcus | 260/483 |
| 3,873,579 | 3/1975 | Rosher | 260/349 |
| 4,020,176 | 4/1977 | Greenwald | 260/349 |
| 4,085,123 | 4/1978 | Flanagan et al. | 149/92 X |
| 4,141,910 | 2/1979 | Flanagan et al. | 149/88 X |

OTHER PUBLICATIONS

Boyer et al.; Chemical Reviews; 54; (1954), pp. 5, 6, 48.

*Primary Examiner*—Joseph Paul Brust
*Attorney, Agent, or Firm*—Donald J. Singer; William J. O'Brien

[57] ABSTRACT

This invention involves the synthesis of a novel family of azido esters and their utilization as energetic plasticizers for advanced solid propellant compositions. This family includes as an illustrative member, the novel compound 6-azidohexyl-6-azidohexanoate.

1 Claim, No Drawings

AZIDO ESTERS

STATEMENT OF GOVERNMENT INTEREST

The invention described herein may be manufactured and used by or for the Government for governmental purposes without the payment of any royalty thereon.

BACKGROUND INFORMATION

This invention relates to solid propellant compositions and to a novel family of plasticizers for use therewith. In a more specific aspect, this invention concerns itself with the use of a novel family of azido esters as energetic plasticizers for advanced solid propellant compositions. In still another specific aspect, this invention concerns itself with the use of azido esters as a means of reducing or minimizing the amount of flame in the exhaust gases generated during the operational phase of gun, missile and rocket propellants.

The increased utilization of propellant compositions for guns, rockets and missiles has spawned a considerable research effort in an attempt to improve their performance characteristics. Generally, solid propellants consist of one or more organic or inorganic oxidizers dispersed in a resinous binder matrix which may also function as a fuel. Typical oxidizers are ammonium perchlorate or HMX (cycloetetramethylene tetranitramine), both of which are well known in the art. Various resinous components, such as hydrocarbons, polyesters, polyurethanes and other like materials may serve as the binder/fuel matrix. A supplemental fuel component, such as finely powered aluminum, may be used also. Other additive components, such as anti-oxidants, burning rate modifiers, wetting agents, anti-foaming agents and plasticizers may be added to the propellant composition, if desired. Dibutylphthalate or triacetin are generally employed as inert plasticizers in combination with the resinous binder material.

In using solid propellants, however, a problem exists in that an undesirable amount of flame is often produced in the exhaust gases emanating from the burning propellant during propulsion. Excessive amounts of flame are extremely undesirable in the exhaust gases since this provides data which pinpoints the sites from which the guns, missiles or rockets are being fired. As a consequence, a continuing research effort has been maintained in an attempt to provide a propellant with a minimum amount of flame in the propellant's exhaust gases.

In furthering the research effort referred to above, it was unexpectedly discovered that a new family of azido esters could be employed as energetic plasticizers in the fabrication of reduced flame temperature gun propellant systems. These novel plasticizers replace the conventional inert plasticizers utilized in conventional composite propellants. The resulting propellant produces a minimum amount of flame during propulsion.

SUMMARY OF THE INVENTION

In accordance with this invention, there is provided a novel family of azido esters which are energetic liquids and find particular utility as energetic plasticizers in advance solid propellants. 6-Azidohexyl-6-azidohexanoate (AHAH) is an example of this family azido esters which have been found to be unexpectedly effective in overcoming the problem of flame in the exhaust gases produced during the operational phase of solid propellant compositions. The energetic plasticizers of this invention replace the conventional inert plasticizers and are used in the propellant in a ratio of from about 1.5 to 4.0 parts of plasticizer to about 1.0 part of binder.

Accordingly, the primary object of this invention is to provide a novel family of azido esters.

Another object of this invention is to provide a novel solid propellant composition that produces only minimum amounts of flame during its propulsion phase.

Still another object of this invention is to provide a novel family of azido esters that find particular utility as energetic plasticizers for advanced solid propellant compositions.

The above and still other objects, and advantages of the present invention will become more readily apparent upon consideration of the following detailed description thereof.

DESCRIPTION OF THE PREFERRED EMBODIMENT

With the above-mentioned and other objects in mind, the present invention contemplates the synthesis of a novel family of azido esters and their utilization as energetic plasticizers in a conventional solid propellant. This novel family of azido esters includes, as a typical illustration, the novel compound 6-azidohexyl-6-azidohexanoate (AHAH). The AHAH compound possesses physical properties that make it suitable for plasticizer use and is considerably more attractive than a conventional plasticizer such as triacetin, dibutyl phthalate or (2,2,2-fluorodinitroethyl) formal (FEFO).

The synthesis of 6-azidohexyl-6-azidohexanoate (AHAH) is accomplished as shown by the following equation:

$$Br(CH_2)_5CO_2(CH_2)_6Cl + 2NaN_3 \rightarrow N_3(CH_2)_5CO_2(CH_2)_6N_3 \qquad (I)$$

Example 1 discloses the experimental details of the reaction illustrated by equation (I).

EXAMPLE 1

6-Azidohexyl-6-azidohexanoate (AHAH)

A mixture of 10.8 g (0.034 mole) of 6-chlorohexyl-6-bromohexanoate, 6.7 g (0.103 mole) of NaN$_3$, and 100 ml of DMF was heated at 80° C. for 16 hours. After cooling the DMF was removed via centrifugation. The solvent was then removed yielding 9.6 g (99% yield) of crude AHAH. Pure AHAH was obtained via liquid chromatography using silica gel as the adsorbent. Its structure was confirmed by ir, gc, and elemental analyses:

Elemental Analyses:

|  |  |  | C | H | N |
|---|---|---|---|---|---|
| Calculated for | C$_{12}$H$_{22}$N$_6$O$_2$ | (%) | 51.04 | 7.86 | 29.77 |
|  | Found | (%) | 50.51 | 7.78 | 29.33 |

An illustration showing the use of the novel energetic liquid plasticizer of this invention in a typical solid propellant is shown in Table I. Although an HMX oxidizer and a polyester resin binder are preferred, other conventional oxidizing and resinous binders may be utilized, if desired, as well as other fuel components, such as powdered aluminum.

Solid propellant compositions are well known and since the basic preparation and constituent ingredients of the propellant compositions of this invention are not significantly altered or critical to the execution of the invention, with the exception of the energetic plasticizer component, a detailed explanation of the propellants preparation is not deemed necessary.

The plastizizers of this invention are liquid in nature and are incorporated into the solid propellant mix in a conventional manner at any stage of processing prior to cure. Generally, however, it is incorporated into the propellant mix before all the solid ingredients have been added. The resulting solid propellant differs from a conventional composition only in the essential replacement of the typical inert plasticizer with the novel energetic plasticizers of this invention.

TABLE I

| Propellant Composition | (Weight %) |
|---|---|
| HMX | 75 |
| Polyester resin | 10 |
| AHAH | 15 |

The ratio of plasticizer to binder of 1.5 to 1.0 can be increased up to about 4.0 to 1.0, if desired.

While the present invention has been described by reference to a particular embodiment thereof, it should be understood by those skilled in the art that all the modifications that are encompassed within the scope of the appended claims are intended to be included herein.

What is claimed is:
1. The compound, 6-azidohexyl-6-azidohexanoate.

* * * * *